United States Patent
Taya (10) Patent No.: US 9,420,942 B2
(45) Date of Patent: Aug. 23, 2016

(54) ENDOSCOPE CLEANING/DISINFECTING APPARATUS

(71) Applicant: OLYMPUS CORPORATION, Tokyo (JP)

(72) Inventor: Naoya Taya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/865,846

(22) Filed: Sep. 25, 2015

(65) Prior Publication Data

US 2016/0007844 A1 Jan. 14, 2016

Related U.S. Application Data

(63) Continuation of application No. PCT/JP2014/074573, filed on Sep. 17, 2014.

(30) Foreign Application Priority Data

Mar. 28, 2014 (JP) ................................. 2014-069675

(51) Int. Cl.
*A61L 2/24* (2006.01)
*A61B 1/12* (2006.01)

(52) U.S. Cl.
CPC . *A61B 1/123* (2013.01); *A61B 1/12* (2013.01); *A61L 2/24* (2013.01)

(58) Field of Classification Search
CPC .......... A61B 1/123; A61B 1/125; A61L 2/24; A61L 2/18; A61L 2202/24
USPC ........ 134/18, 113, 57 R, 200, 58 R; 422/119, 422/105, 67, 108, 116; 49/31, 13; 116/200
See application file for complete search history.

(56) References Cited

U.S. PATENT DOCUMENTS 8,034,193 B2 * 10/2011 Suzuki ................... A61B 1/123
134/166 C
2009/0065034 A1 3/2009 Suzuki et al.

FOREIGN PATENT DOCUMENTS

EP 1 875 856 A1 1/2008
JP 10-248910 A 9/1998
(Continued)

OTHER PUBLICATIONS

Mori, Yasunori et al., "Electronic Endoscopic Equipment" Aug. 2003, JP 2003-235793 Machine Translation.*

*Primary Examiner* — David Cormier
*Assistant Examiner* — Thomas Bucci
(74) *Attorney, Agent, or Firm* — Scully, Scott, Murphy & Presser, P.C.

(57) ABSTRACT

An endoscope cleaning/disinfecting apparatus includes: a cleaning/disinfecting tank, a lid portion, an accommodation detecting section, an opening/closing detecting section, a cleaning/disinfecting section, a cleaning/disinfection detecting section, an informing section, a judging section judging a case where the opening/closing detecting section detects a closed state of the lid portion before the cleaning/disinfection detecting section detecting driving of the cleaning/disinfecting section after the accommodation detecting section detecting that an endoscope is accommodated in the cleaning/disinfecting tank as a first closed state; and a control section performing control of driving the informing section to issue a warning when the opening/closing detecting section detects an opened state of the lid portion before the cleaning/disinfection detecting section detecting driving of the cleaning/disinfecting section after the judging section detecting the first closed state.

2 Claims, 9 Drawing Sheets

(56) References Cited

FOREIGN PATENT DOCUMENTS

| JP | 2003-235793 | A | | 8/2003 |
| JP | 2003235793 | A | * | 8/2003 |
| JP | 2006-230492 | A | | 9/2006 |
| JP | 2006-296982 | A | | 11/2006 |
| JP | 2009-45132 | A | | 3/2009 |
| WO | WO 2006/115177 | A1 | | 11/2006 |

* cited by examiner

ENDOSCOPE CLEANING/DISINFECTING APPARATUS

CROSS REFERENCE TO RELATED APPLICATION

This application is a continuation application of PCT/JP2014/074573 filed on Sep. 17, 2014 and claims benefit of Japanese Application No. 2014-069675 filed in Japan on Mar. 28, 2014, the entire contents of which are incorporated herein by this reference.

BACKGROUND OF THE INVENTION

1. Field of the Invention

The present invention relates to an endoscope cleaning/disinfecting apparatus for cleaning/disinfecting an endoscope.

2. Description of the Related Art

At a time of cleaning/disinfecting an endoscope using an endoscope cleaning/disinfecting apparatus, an operator first opens a lid portion of the endoscope cleaning/disinfecting apparatus, accommodates a used endoscope in a cleaning/disinfecting tank and connects various tubes to a pipe sleeve of the endoscope, and, after that, the operator closes the lid portion and presses a start button.

After that, a cleaning/disinfecting process starts. After a predetermined time period elapses, the cleaning/disinfecting process ends. Lastly, the operator opens the lid portion and takes out the cleaned/disinfected endoscope.

Here, in the cleaning/disinfecting process described above, after the used endoscope is accommodated in the cleaning/disinfecting tank, and the lid portion is closed, the endoscope may be left as it is for a long time without the start button being pressed.

In this case, there is a possibility that an operator different from the operator who accommodated the endoscope in the cleaning/disinfecting tank opens the lid portion and takes out the endoscope which has not been cleaned/disinfected. Therefore, there has been a demand for a function of informing the operator who has taken out the endoscope from the cleaning/disinfecting tank that the endoscope has not been cleaned/disinfected.

In view of such a situation, Japanese Patent Application Laid-Open Publication No. 2003-235793 discloses a system in which, by an endoscope cleaning/disinfecting apparatus having a function of transmitting information to the effect that an endoscope has been cleaned/disinfected to the endoscope after a cleaning/disinfecting process ends, and a microcomputer in a processor having a function of, when an endoscope is connected to the processor in an operating room at a time of using the endoscope, receiving the information whether the endoscope has been cleaned/disinfected or not from the endoscope, and giving a warning if an endoscope which has not been cleaned/disinfected is connected, an operator is informed that an endoscope has not been cleaned/disinfected.

SUMMARY OF THE INVENTION

An endoscope cleaning/disinfecting apparatus in an aspect of the present invention is provided with: a cleaning/disinfecting tank in which an endoscope is accommodated; a lid portion openable/closable relative to the cleaning/disinfecting tank; an accommodation detecting section detecting that the endoscope is accommodated in the cleaning/disinfecting tank; an opening/closing detecting section detecting an opened state and a closed state of the lid portion relative to the cleaning/disinfecting tank; a cleaning/disinfecting section for performing cleaning/disinfection of the endoscope in the cleaning/disinfecting tank; a cleaning/disinfection detecting section detecting driving of the cleaning/disinfecting section; an informing section issuing a warning; a judging section connected to the accommodation detecting section, the opening/closing detecting section and the cleaning/disinfection detecting section, the judging section judging a case where the opening/closing detecting section detects the closed state of the lid portion before the cleaning/disinfection detecting section detects driving of the cleaning/disinfecting section and after the accommodation detecting section detects that the endoscope is accommodated in the cleaning/disinfecting tank as a first closed state; and a control section connected to at least the opening/closing detecting section, the cleaning/disinfection detecting section, the informing section and the judging section, the control section performing control of driving the informing section to issue a warning when the opening/closing detecting section detects the opened state of the lid portion before the cleaning/disinfection detecting section detects driving of the cleaning/disinfecting section after the judging section detects the first closed state.

DETAILED DESCRIPTION OF THE PREFERRED EMBODIMENT

Embodiments of the present invention will be described below with reference to drawings. Note that the drawings are schematic, and a relationship between thickness and width of each of members, a thickness ratio of the respective members and the like are different from actual ones. It goes without saying that parts which are mutually different in a dimension relationship or ratio are included among the drawings.

First Embodiment

Figure 1:
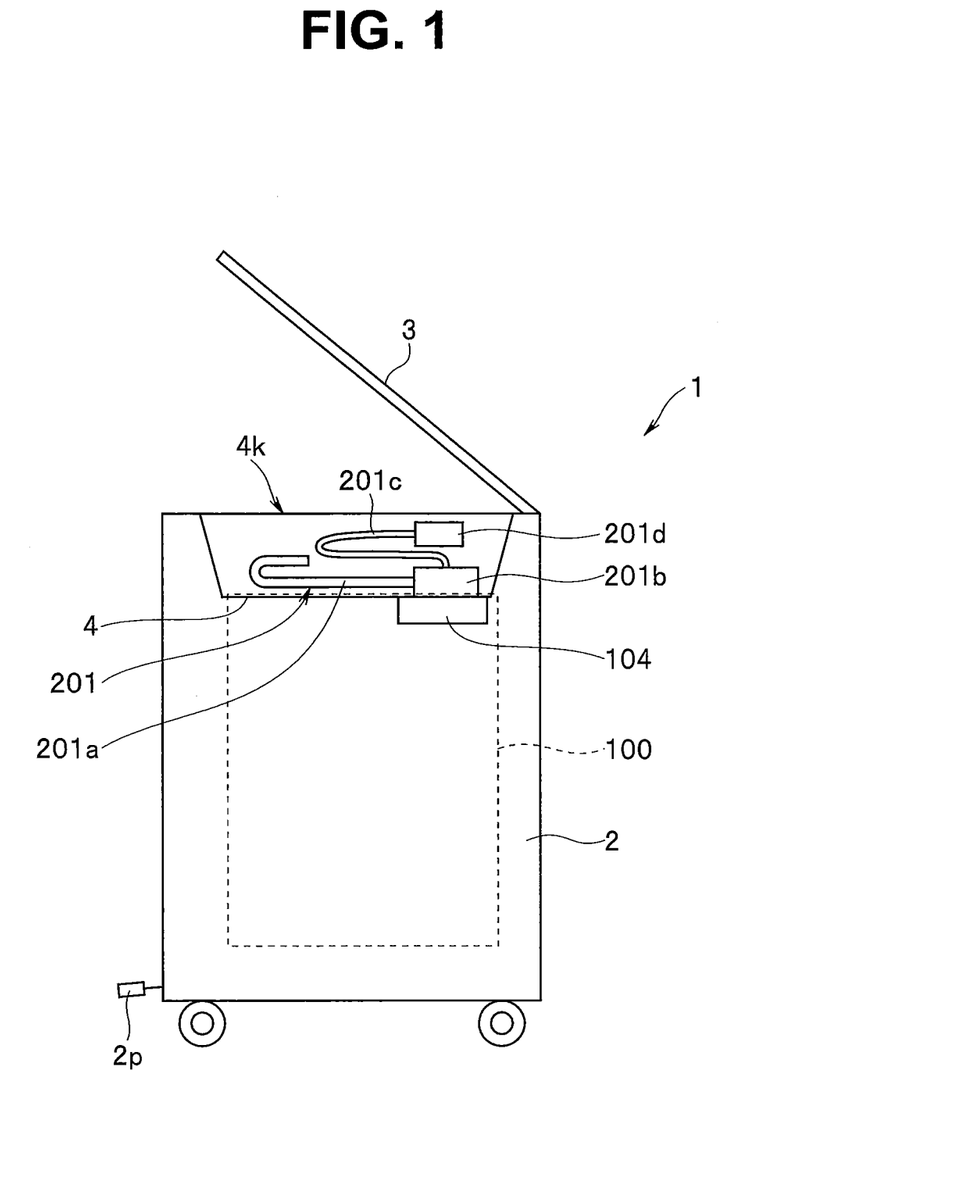
FIG. 1 is a diagram schematically showing an endoscope cleaning/disinfecting apparatus of a first embodiment.
Figure 2:
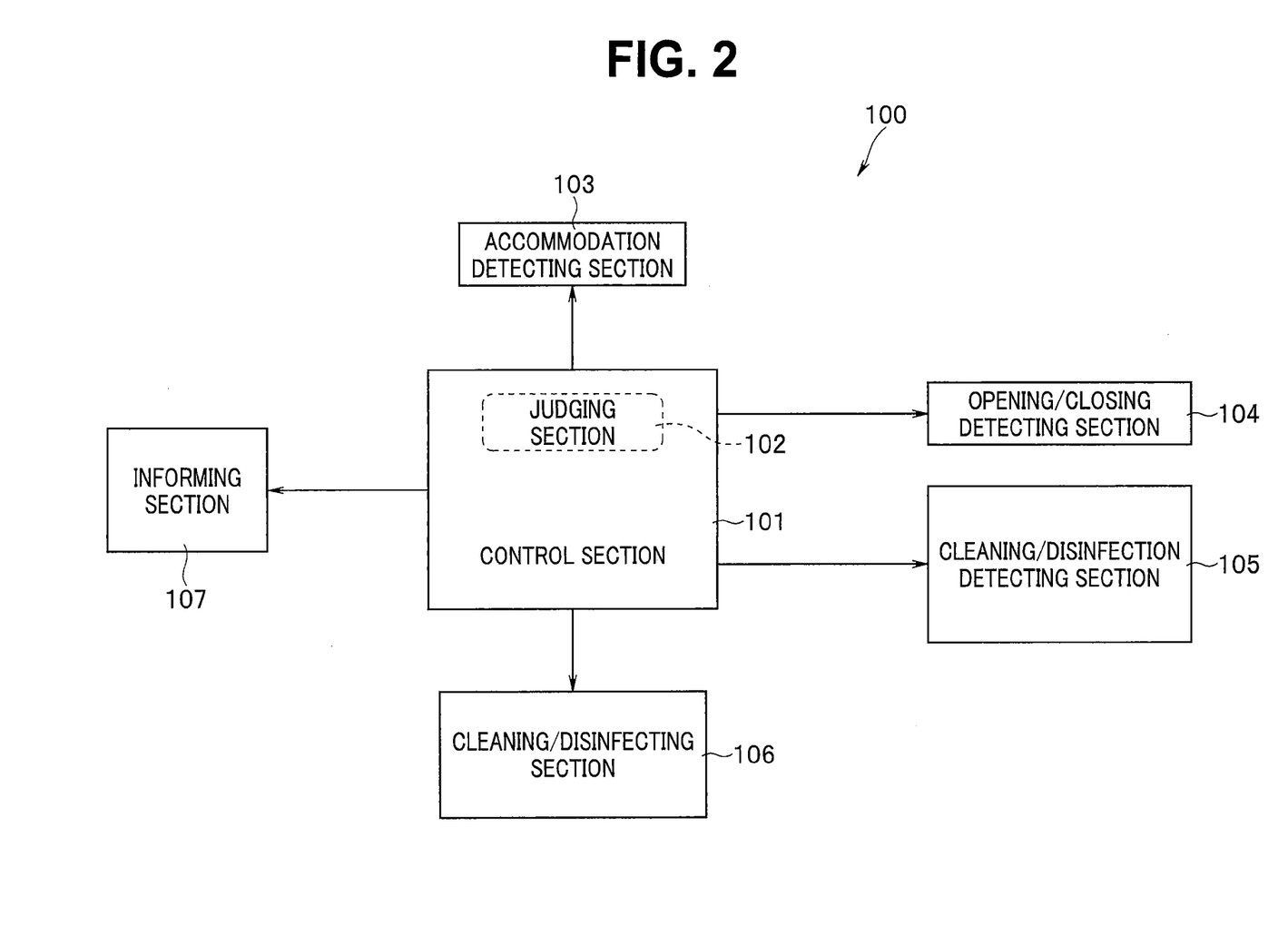
FIG. 2 is a block diagram schematically showing a warning section in an apparatus body of the endoscope cleaning/disinfecting apparatus of FIG. 1.

FIG. 1 is a diagram schematically showing an endoscope cleaning/disinfecting apparatus of the present embodiment. FIG. 2 is a block diagram schematically showing a warning section in an apparatus body of the endoscope cleaning/disinfecting apparatus of FIG. 1.

Figure 3:
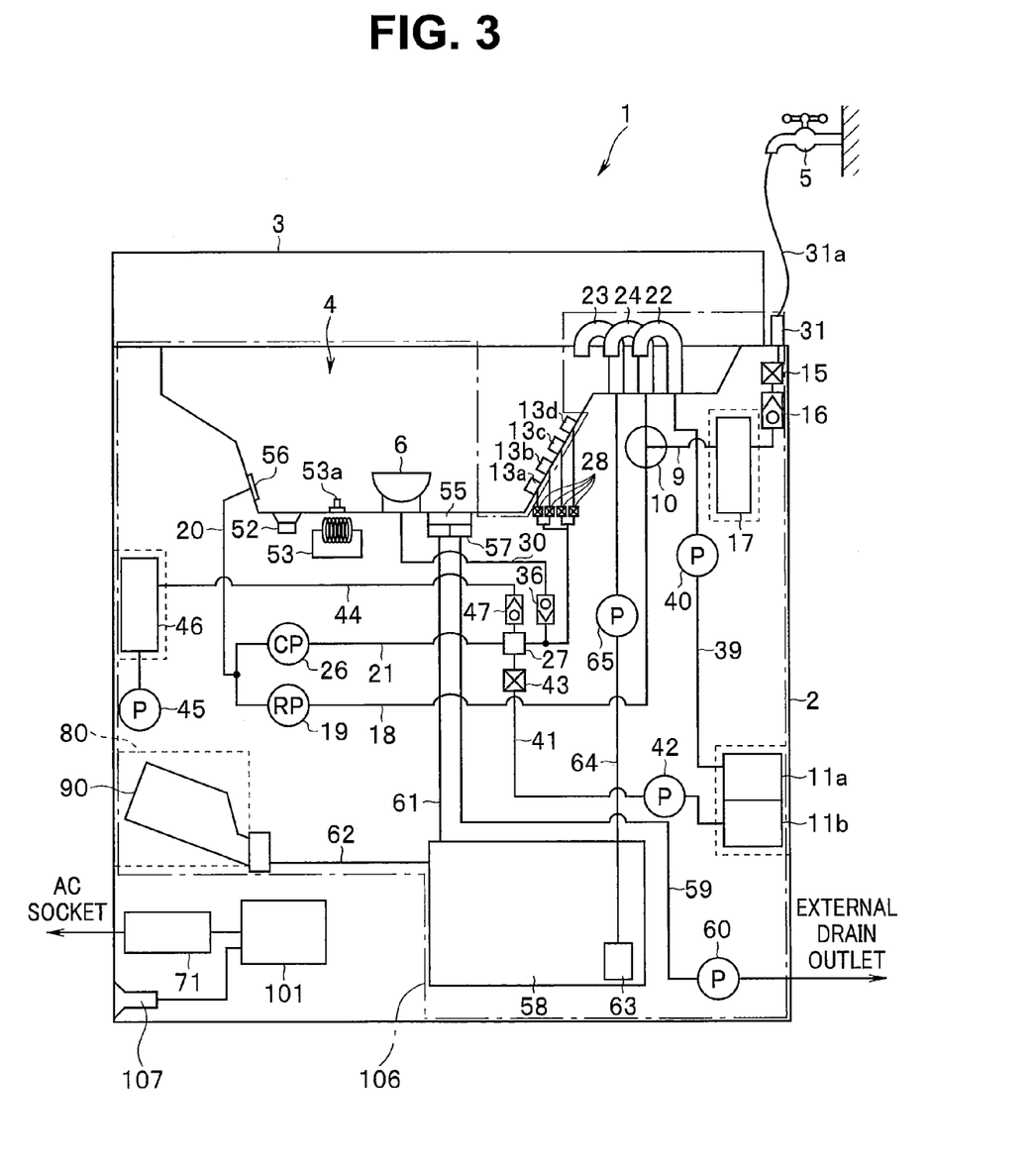
FIG. 3 is a diagram showing an example of a cleaning/disinfecting section in the warning section of FIG. 2 together with an internal configuration of the cleaning/disinfecting apparatus.
Figure 4:
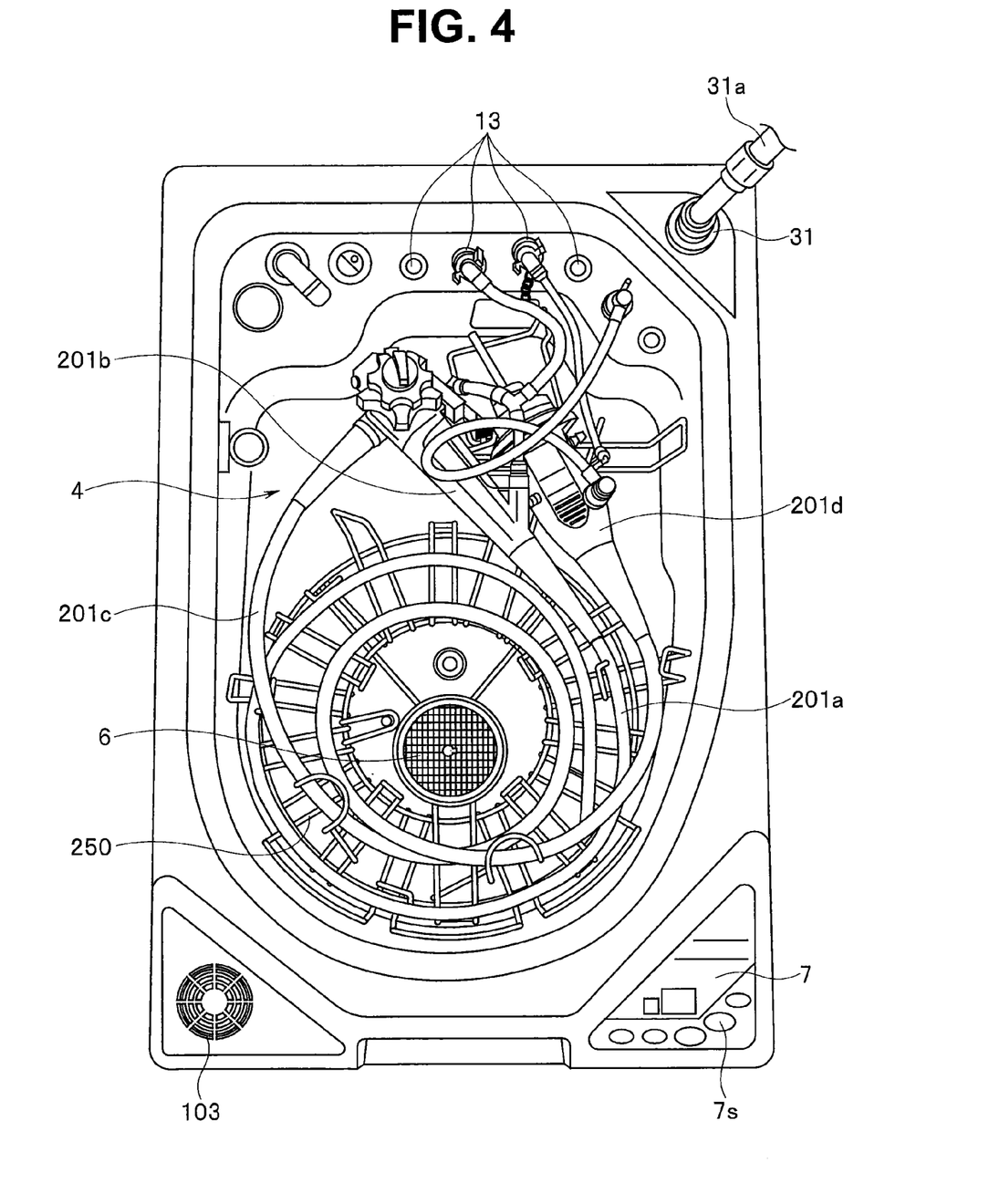
FIG. 4 is a perspective view showing a state that an endoscope is placed and set together with an endoscope guide member in a cleaning/disinfecting tank of the endoscope cleaning/disinfecting apparatus of FIG. 1.

FIG. 3 is a diagram showing an example of a cleaning/disinfecting section in the warning section of FIG. 2 together with an internal configuration of the cleaning/disinfecting apparatus, and FIG. 4 is a perspective view showing a state that an endoscope is placed and set together with an endoscope guide member in a cleaning/disinfecting tank of the endoscope cleaning/disinfecting apparatus of FIG. 1.

As shown in FIG. 1, an endoscope cleaning/disinfecting apparatus 1 is provided with an apparatus body 2, and a lid portion 3 which is openably/closably connected, for example, via a hinge not shown on the apparatus body 2.

A pedal switch 2p for opening the lid portion 3 closed over a top portion of the apparatus body 2 upward from the apparatus body 2 by an operator's stepping operation is provided at a lower portion of the apparatus body 2.

Note that the opening/closing operation of the lid portion 3 is not limited to the pedal switch 2p. For example, the operator may lift the lid portion 3 by hand, or the opening/closing operation may be performed by a switch which is manually operated by the operator.

Further, a cleaning/disinfecting tank 4 in which an endoscope 201 to be cleaned/disinfected with the endoscope cleaning/disinfecting apparatus 1 is to be accommodated is provided on an upper portion of the apparatus body 2. The endoscope 201 is accommodated in the cleaning/disinfecting tank 4, for example, with an endoscope guide member 250 as shown in FIG. 4.

Note that an opening 4k, which is an opening through which the endoscope 201 is accommodated in and taken out from the cleaning/disinfecting tank 4, is freely opened and closed with the lid portion 3. Note that opened/closed states of the lid portion 3 are detected by an opening/closing detecting section 104 (see FIG. 2) to be described later.

In the present embodiment, a case where one endoscope 201 is accommodated in the cleaning/disinfecting tank 4, and the one endoscope 201 is cleaned/disinfected with the endoscope cleaning/disinfecting apparatus 1 is shown as an example. Note that the case is not limiting. A configuration is also possible in which two or more endoscopes are accommodated in the cleaning/disinfecting tank 4 and cleaned/disinfected at the same time.

Further, main portions of the endoscope 201 are configured with, for example, an insertion portion 201a to be inserted into a subject, an operation portion 201b connectedly provided at a proximal end of the insertion portion 201a, a universal cord 201c extended from the operation portion 201b, and a connector portion 201d provided at an extended end of the universal cord 201c.

Note that detection of the endoscope 201 having been accommodated in the cleaning/disinfecting tank 4 is performed by an accommodation detecting section 103 (see FIG. 2) to be described later.

Further, a warning section 100 is provided inside the apparatus body 2. As shown in FIG. 2, the warning section 100 is provided with: the accommodation detecting section 103 which detects that the endoscope 201 is accommodated in the cleaning/disinfecting tank 4, the opening/closing detecting section 104 which detects the opened and closed states of the lid portion 3 relative to the cleaning/disinfecting tank 4, a cleaning/disinfecting section 106 for performing cleaning/disinfection of the endoscope 201 in the cleaning/disinfecting tank 4, a cleaning/disinfection detecting section 105 which detects driving of the cleaning/disinfecting section 106, an informing section 107 which issues a warning, a control section 101 provided with a judging section 102.

Note that the control section 101 is connected to at least the opening/closing detecting section 104, the cleaning/disinfecting section 106 and the informing section 107 and also connected to the accommodation detecting section 103.

The accommodation detecting section 103 is provided, for example, on a top surface of the apparatus body 2 as shown in FIG. 4, and the accommodation detecting section 103 detects that the endoscope 201 is accommodated in the cleaning/disinfecting tank 4.

Note that the accommodation detecting section 103 may be provided on another region of the cleaning/disinfecting tank 4 or the endoscope cleaning/disinfecting apparatus 1.

Further, the accommodation detecting section 103 is configured, for example, with an RF-ID reader, a barcode reading section or a touch panel portion on which input is performed by the operator.

Note that FIG. 4 shows a case where the accommodation detecting section 103 is configured with an RF-ID reader as an example.

Therefore, in the case where the accommodation detecting section 103 is configured with an RF-ID reader, a known RF-ID not shown is included in the connector portion 201d so as to detect the endoscope 201 being accommodated in the cleaning/disinfecting tank 4.

In the RF-ID, information about the endoscope 201, such as a model name and a serial number of the endoscope 201, is inputted. Note that, if the RF-ID is not included in the connector portion 201d, an RF-ID tag or an RF-ID seal may be externally attached to the connector portion 201d. Further, the RF-ID may be provided on another region of the endoscope 201 without being limited to the connector portion 201d.

In the case where the accommodation detecting section 103 is an RF-ID reader, the accommodation detecting section 103 detects that the endoscope 201 is accommodated in the cleaning/disinfecting tank 4 by reading information in the RF-ID, by the connector portion 201d being brought near to the accommodation detecting section 103 by the operator.

Note that the above is same for a case where the accommodation detecting section 103 is configured with a barcode reading section. In this case, the connector portion 201d is provided with a barcode in which various information about the endoscope 201 is inputted.

In this case, the accommodation detecting section 103 detects that the endoscope 201 is accommodated in the cleaning/disinfecting tank 4 by reading information in the barcode, by the connector portion 201d being brought near to the accommodation detecting section 103 by the operator.

Further, in a case where the accommodation detecting section 103 is configured with a touch panel portion, the accommodation detecting section 103 detects that the endoscope 201 is accommodated in the cleaning/disinfecting tank 4 by input being performed on the touch panel portion by the operator.

The opening/closing detecting section 104 detects the opened state and the closed state of the lid portion 3 relative to the cleaning/disinfecting tank 4, and the opening/closing detecting section 104 is provided, for example, in the apparatus body 2. Further, the opening/closing detecting section 104 is configured with a known opening/closing detecting sensor.

For example, the cleaning/disinfecting section 106 has a chemical storing section storing chemical liquid and a chemical supplying section which supplies the chemical liquid stored in the chemical storing section to the cleaning/disinfecting tank 4 as minimum components. Note that the chemical liquid stated here may be cleaning liquid which removes organic stains adhering to an endoscope or may be disinfectant liquid which detoxifies fungi adhering to an endoscope.

For example, the chemical storing section may include one or more kinds among a detergent tank 11a, an alcohol tank 11b and a chemical tank 58 which are to be described below in detail. Furthermore, for example, the chemical supplying section may include one or more kinds among a detergent conduit 39 and a detergent pump, an alcohol conduit 41 and an alcohol supplying pump 42, or a chemical conduit 64 and a chemical pump 65.

As an example, the cleaning/disinfecting section 106 is configured with a region indicated by a dot-and-dash line in FIG. 3. An example of an internal configuration of the endoscope cleaning/disinfecting apparatus 1 will be shown below.

As shown in FIG. 3, the endoscope cleaning/disinfecting apparatus 1 has a configuration in which tap water is supplied by one end of a water supply hose 31a being connected to a water supply hose connection port 31 and the other end of the water supply hose 31a being connected to a tap faucet 5.

The water supply hose connection port 31 is communicated with one end of a water supply conduit 9. The other end of the water supply conduit 9 is connected to a three-way solenoid valve 10, and a water supply solenoid valve 15, a check valve 16 and a water supply filter 17 are disposed midway in the water supply conduit 9 in that order from the water supply hose connection port 31 side.

Note that the water supply filter 17 is configured as a cartridge-type filtration filter so that it can be periodically exchanged. The water supply filter 17 removes foreign matters, germs and the like in tap water passing through the water supply filter 17.

The three-way solenoid valve 10 is connected to one end of a flow liquid conduit 18 and switches between communication with the water supply conduit 9 and communication with the flow liquid conduit 18 relative to a water supply circulation nozzle 24.

That is, the water supply circulation nozzle 24 is communicated with either the water supply conduit 9 or the flow liquid conduit 18 by a switching operation of the three-way solenoid valve 10. Further, a flow liquid pump 19 is disposed on the other end side of the flow liquid conduit 18.

A circulation port 56 arranged on the cleaning/disinfecting tank 4 is connected to one end of a circulation conduit 20. The other end of the circulation conduit 20 branches into two so as to be communicated with the other end of the flow liquid conduit 18 and one end of a channel conduit 21. The other end of the channel conduit 21 is communicated with respective air/water feeding and forceps ports 13a to 13d. Further, the other end of the channel conduit 21 is also communicated with a forceps raising port not shown, though it is not shown.

Midway along the channel conduit 21, a channel pump 26, a channel block 27 and a channel solenoid valve 28 are disposed, respectively, in that order from one end side of the channel conduit 21. The other end of a case conduit 30 one end of which is connected to a cleaning case 6 is connected to the channel conduit 21 between the channel block 27 and the channel solenoid valve 28. A relief valve 36 is disposed in the case conduit 30.

A cleaning nozzle 22 is connected to one end of the detergent conduit 39, and the other end of the detergent conduit 39 is connected to the detergent tank 11a. A detergent pump 40 configured with a high-pressure self-priming pump is disposed midway along the detergent conduit 39 in order to lift detergent from the detergent tank 11a to the cleaning/disinfecting tank 4.

The alcohol tank 11b is connected to one end of the alcohol conduit 41, and the alcohol conduit 41 is connected to the channel block 27 so as to be predeterminedly communicated with the channel conduit 21.

The high-pressure alcohol supplying pump 42 and a solenoid valve 43 are disposed in the alcohol conduit 41 in order to lift alcohol from the alcohol tank 11b to the cleaning/disinfecting tank 4.

Further, one end of an air conduit 44 for supplying air from an air pump 45 configured with a self-priming pump capable of transferring gas is connected to the channel block 27 so as to be predeterminedly communicated with the channel conduit 21.

The other end of the air conduit 44 is connected to the air pump 45, and a check valve 47 and an air filter 46 which is periodically exchanged are disposed at midway positions in the air conduit 44.

An openable/closable switching valve 57 for draining the detergent and the like to an outside or recovering the disinfectant liquid to the chemical tank 58 by a switching operation of the valve is arranged in a drain outlet 55 of the cleaning/disinfecting tank 4.

The switching valve 57 is connected to the other end of a drain conduit 59 which is communicated with a drain hose not shown, which is connected to an external drain outlet, by one end being connected to the drain hose, and a drain pump 60 is disposed on the drain conduit 59.

Further, the switching valve 57 is connected to one end of a chemical recovery conduit 61, and the other end of the chemical recovery conduit 61 is connected to the chemical tank 58.

The chemical tank 58 is also connected to one end of a chemical receiving section 62 so that chemical liquid, for example, disinfectant liquid is supplied from a chemical bottle 90 as described above. The other end of the chemical receiving section 62 is predeterminedly connected to a cassette tray 80 onto which the chemical bottle 90 is to be accommodated.

Further, one end portion of the chemical conduit 64 with a suction filter 63 provided at one end is predeterminedly accommodated in the chemical tank 58. The other end of the chemical conduit 64 is connected to a disinfectant liquid nozzle 23, and the chemical pump 65 configured with a high-pressure pump is disposed at a midway position in order to lift the disinfectant liquid from the chemical tank 58 to the cleaning/disinfecting tank 4.

Note that, for example, two ultrasound transducers 52 and a heater 53 are arranged at a portion lower than a bottom surface of the cleaning/disinfecting tank 4, as described above. Further, a temperature detection sensor 53a is provided almost at a center of the bottom surface of the cleaning/disinfecting tank 4 to adjust temperature of the heater 53.

The heater 53 is for heating the disinfectant liquid which is stored in the cleaning/disinfecting tank 4 and circulates in the apparatus, to a predetermined temperature. Note that there is a temperature appropriate for disinfectant liquid from which a disinfectant effect thereof can be expected most. The disinfectant liquid heated to the predetermined temperature, which is the appropriate temperature, by the heater 53 can effectively disinfect outer surfaces in the endoscope 201 and the apparatus body 2, and each conduit.

Further, the temperature detection sensor 53a detects a liquid temperature of the disinfectant liquid which is stored in the cleaning/disinfecting tank 4 and circulates in the apparatus, and transmits a result of the detection to the control section 101. Then, the control section 101 performs control of driving or stopping the heater 53 so as to keep the disinfectant liquid at the predetermined temperature on a basis of the detection result from the temperature detection sensor 53a.

Further, a power source 71 to which power is supplied from an external AC receptacle and the control section 101 which is electrically connected to the power source 71 are provided inside the endoscope cleaning/disinfecting apparatus 1. The control section 101 is supplied with various signals from a main operation panel 7 (see FIG. 4) and the like and performs drive control of each pump, each solenoid valve and the like described above.

Returning to FIG. 2, the cleaning/disinfection detecting section 105 is for detecting driving of the cleaning/disinfecting section 106 indicated by the dot-and-dash line in FIG. 3, and the cleaning/disinfection detecting section 105 is configured, for example, with a water level sensor, a pressure sensor, a temperature sensor or another sensor.

More specifically, the cleaning/disinfection detecting section 105 detects driving of the cleaning/disinfecting section 106 by detecting supply of liquid into the cleaning/disinfecting tank 4, detecting pressure in the various conduits described above, detecting a temperature of liquid in the cleaning/disinfecting tank 4, detecting driving of the various pumps described above or the like.

The judging section 102 is connected to the accommodation detecting section 103, the opening/closing detecting section 104 and the cleaning/disinfection detecting section 105. The judging section 102 judges a case where the opening/closing detecting section 104 detects the closed state of the lid portion 3 before the cleaning/disinfection detecting section 105 detecting driving of the cleaning/disinfecting section 106 after the accommodation detecting section 103 detecting that the endoscope 201 has been accommodated in the cleaning/disinfecting tank 4, as a first closed state.

Further, though the judging section 102 is integrally provided with the control section 101 in the present embodiment, the judging section 102 may be separately provided.

When the opening/closing detecting section 104 detects the opened state of the lid portion 3 before the cleaning/disinfection detecting section 105 detecting driving of the cleaning/disinfecting section 106 after the judging section 102 detecting the first closed state, the control section 101 performs control of driving the informing section 107 to issue a warning, and the control section 101 is configured, for example, with a CPU.

The informing section 107 issues a warning. The informing section 107 warns the operator that the lid portion 3 has been opened before driving of the cleaning/disinfecting section 106 after the first closed state, for example, by a warning sound, a warning display using the main operation panel 7 or the like, a light, a smell or the like.

Figure 5:
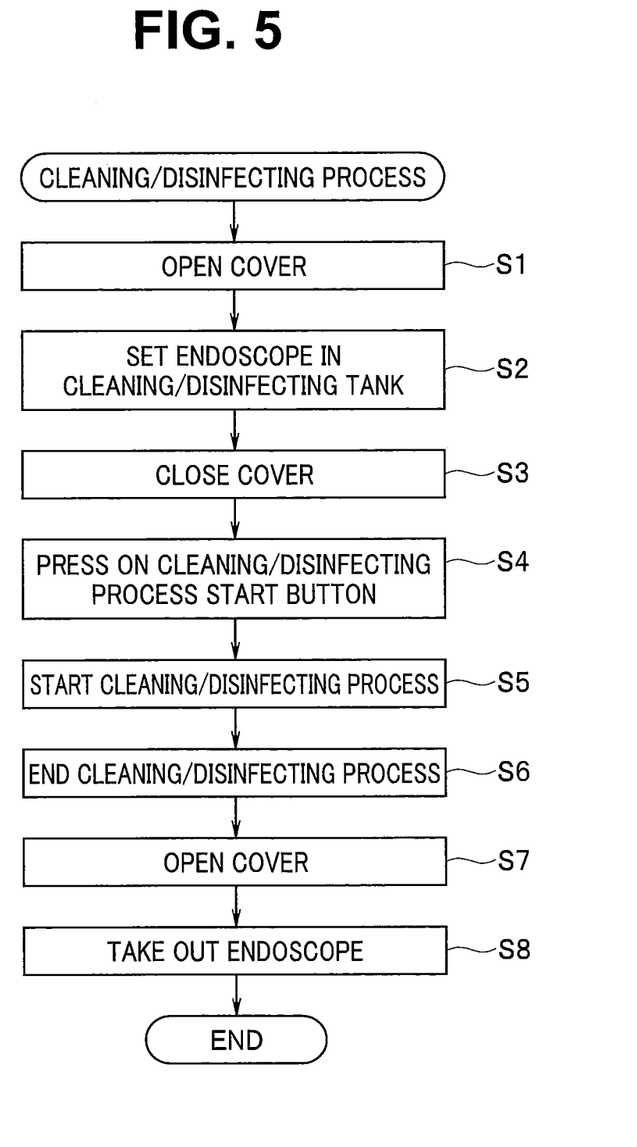
FIG. 5 is a flowchart schematically showing an endoscope cleaning/disinfecting process using the endoscope cleaning/disinfecting apparatus of FIG. 1.

Next, a process for cleaning/disinfecting the endoscope 201 using the endoscope cleaning/disinfecting apparatus 1 of FIG. 1 will be simply described with use of FIG. 5. FIG. 5 is a flowchart schematically showing the endoscope cleaning/disinfecting process using the endoscope cleaning/disinfecting apparatus of FIG. 1.

As shown in FIG. 5, the operator first opens the lid portion 3 by performing an operation of stepping the pedal switch 2p at step S1.

Next, at step S2, by causing the connector portion 201d of the endoscope 201 which has been used to be brought near to the accommodation detecting section 103, the accommodation detecting section 103 is caused to read the RF-ID of the connector portion 201d if the accommodation detecting section 103 is configured with an RF-ID reader. After that, the endoscope 201 is accommodated in the cleaning/disinfecting tank 4 as shown in FIG. 4 described above, and the respective air/water feeding and forceps ports 13a to 13d provided on the cleaning/disinfecting tank 4 and a tube extending from a water leakage detection port not shown are connected to pipe sleeves not shown which are provided on the operation portion 201b and the connector portion 201d to set the endoscope 201.

After that, at step S3, the lid portion 3 is closed by a manual operation. At this time, the closed state of the lid portion 3 is detected by the opening/closing detecting section 104, and the lid portion 3 is judged to be in the first closed state by the judging section 102. Note that, since the lid portion 3 is not locked at this point of time, it is possible to open the lid portion 3 again. That is, the operator can take out the endoscope 201 which has not been cleaned/disinfected, from the cleaning/disinfecting tank 4. This is because there may be a case where the lid portion 3 is opened again after being closed to adjust an arrangement position of the endoscope 201 in the cleaning/disinfecting tank 4 again.

Next, at step S4, a cleaning/disinfecting process start button 7s provided on the main operation panel 7 is pressed on. Note that the lid portion 3 is locked after the cleaning/disinfecting process start button 7s is pressed on, and, until after the cleaning/disinfecting process ends at step S6, it does not happen that the lock is released.

That is, after the cleaning/disinfecting process starts at step S5, the operator cannot take out the endoscope 201 from the cleaning/disinfecting tank 4 until after the end at step S6, unless the power source of the endoscope cleaning/disinfecting apparatus 1 is forcedly turned off.

As a result, the known cleaning/disinfecting process for cleaning/disinfecting the endoscope 201 in the cleaning/disinfecting tank 4 starts at step S5, and the cleaning/disinfecting process ends at step S6 after a predetermined time period elapses. Note that the lock of the lid portion 3 is released after the cleaning/disinfecting process ends.

After that, at step S7, the operator opens the lid portion 3 by performing a stepping operation of the pedal switch 2p and takes out the endoscope 201 which has been cleaned/disinfected from the cleaning/disinfecting tank 4.

Figure 6:
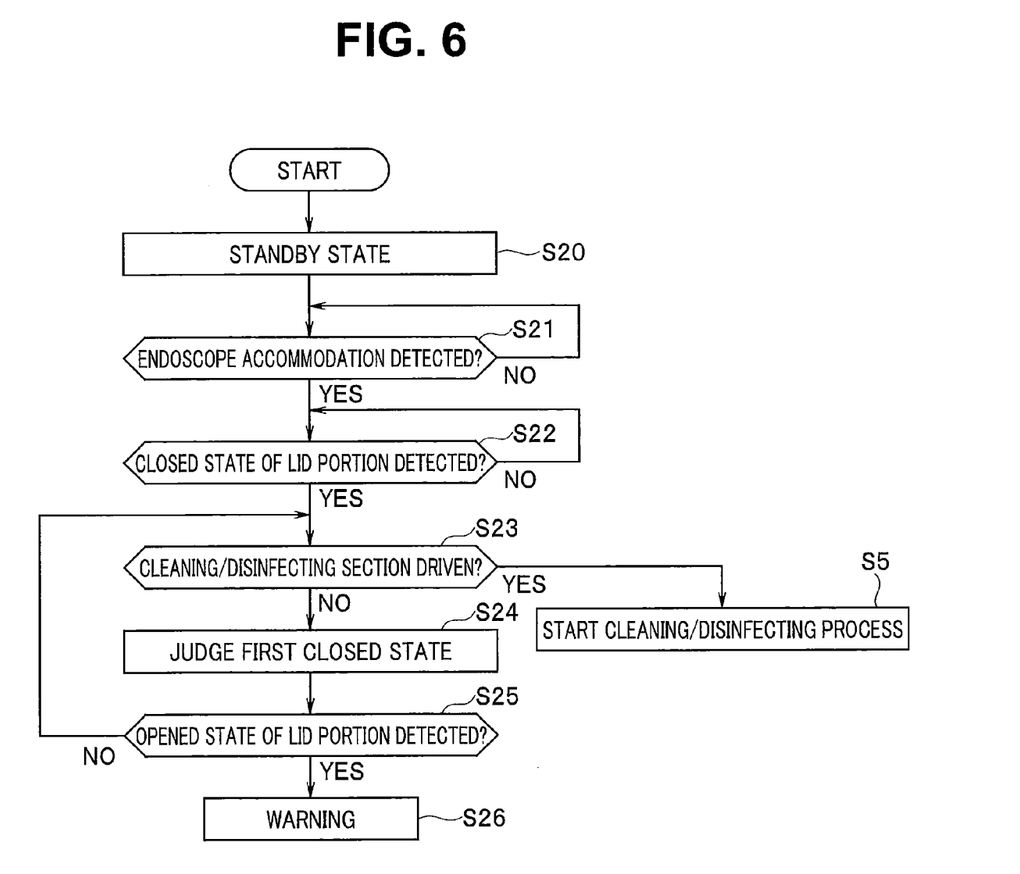
FIG. 6 is a flowchart showing controlling operation for a warning section by a control section of FIG. 2.

Next, an operation of controlling the warning section 100 by the control section 101 of FIG. 2 will be described with use of FIG. 6. FIG. 6 is a flowchart showing controlling operation for the warning section by the control section of FIG. 2.

As shown in FIG. 6, first, in a standby state at step S20 where the accommodation detecting section 103 can detect the endoscope 201, it is judged at step S21 whether the endoscope 201 has been accommodated in the cleaning/disinfecting tank 4 or not, with use of the accommodation detecting section 103, that is; whether the accommodation detecting section 103 has detected the endoscope 201 or not.

More specifically, if the accommodation detecting section 103 is configured with an RF-ID reader, it is judged whether the endoscope 201 has been accommodated or not by whether or not an RF-ID has been read by the connector portion 201d being brought near to the accommodation detecting section 103 by the operator.

If the endoscope 201 is detected, it is judged at step S22 whether the lid portion 3 has been closed or not by the opening/closing detecting section 104.

If the lid portion 3 has been closed, it is judged at step S23 whether or not the cleaning/disinfecting section 106 has been driven with use of the cleaning/disinfection detecting section 105. If the cleaning/disinfecting section 106 has been driven, the process branches to step S5, where the cleaning/disinfecting process described above is started. If the cleaning/disinfecting section 106 has not been driven, the process transitions to step S24, where it is judged by the judging section 102 that the lid portion 3 is in the first closed state. After that, the process transitions to step S25.

At step S25, it is judged by the control section 101 whether the opened state of the lid portion 3 has been detected by the opening/closing detecting section 104 or not. If the lid portion 3 is still in the closed state, the process returns to step S23. If the opened state is detected, the informing section 107 is driven to issue a warning, and the operator is warned that the lid portion 3 has been opened by an operation of stepping the pedal switch 2p being performed before driving of the cleaning/disinfecting section 106 after the first closed state, at step S26 lastly.

Thus, in the present embodiment, it is shown that, when it is detected that the endoscope 201 is accommodated in the cleaning/disinfecting tank 4, and the opened state of the lid portion 3 is detected by the opening/closing detecting section 104 before driving of the cleaning/disinfecting section 106, after the first closed state being detected by the judging section 102 before driving of the cleaning/disinfecting section 106, the control section 101 drives the informing section 107 to issue a warning.

Thus, when, before the cleaning/disinfecting process is started, the lid portion 3 is opened to take out the endoscope 201 in a state that the endoscope 201 is accommodated in the cleaning/disinfecting tank 4, a warning is necessarily issued. Therefore, it is possible to cause the operator to easily recognize that the endoscope he/she is going to take out from the cleaning/disinfecting tank 4 has not been cleaned/disinfected.

Further, since it is possible to issue a warning using a configuration of an existing endoscope cleaning/disinfecting apparatus, increase in manufacturing cost is not caused.

From the above, it is possible to provide the endoscope cleaning/disinfecting apparatus 1 provided with a configuration capable of preventing the endoscope 201 which has not been cleaned/disinfected from being taken out from the cleaning/disinfecting tank 4 by the operator.

Figure 7:
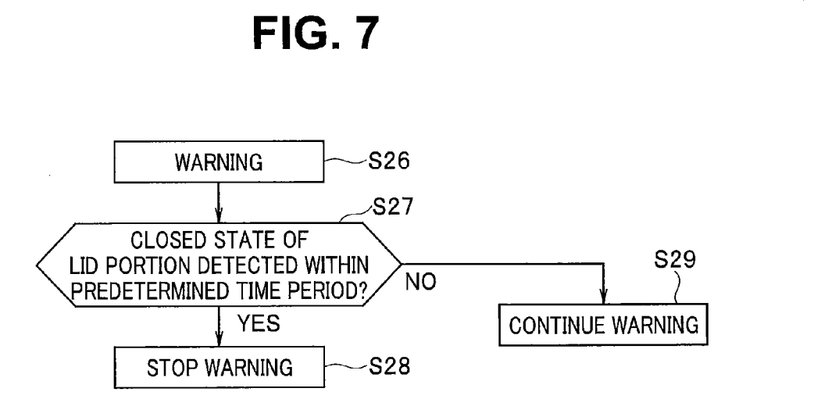
FIG. 7 is a flowchart showing a variation of controlling operation for the warning section by the control section of FIG. 2 in a case where the endoscope is detected again within a predetermined time period after a warning step of FIG. 6.

Note that a variation will be shown below with use of FIG. 7. FIG. 7 is a flowchart showing a variation of controlling operation for the warning section by the control section of FIG. 2 in a case where the endoscope is detected again in a predetermined time period after a warning step of FIG. 6.

In the embodiment described above, it is shown that, when the lid portion 3 is opened before driving of the cleaning/disinfecting section 106 after the first closed state being judged by the judging section 102, the informing section 107 issues a warning.

However, there may be a case where, before the cleaning/disinfecting process start button 7s is pressed on at step S4 after the lid portion 3 being closed at step S3 of FIG. 5, the lid portion 3 is opened again to adjust the arrangement position of the endoscope 201 in the cleaning/disinfecting tank 4 again as described above.

At this time, when the lid portion 3 is opened, a warning is issued. After that, when the endoscope 201 is reset in the cleaning/disinfecting tank 4, and the lid portion 3 is closed, the warning is continuously issued. Therefore, there is a problem that usability is bad for the operator.

Therefore, after a warning is issued from the informing section 107 at step S26 when the lid portion 3 is opened for reset at step S25 before the cleaning/disinfecting process start button 7s being pressed on, after the judgment of the first closed state at step S24 of FIG. 6, the control section 101 may transition to step S28 and perform control of stopping the warning if the closed state of the lid portion 3 is detected within a predetermined time period at step S27 or may perform control of continuing the warning at step S29 if it is not possible to detect the closed state of the lid portion 3 within the predetermined time period, as shown in FIG. 7.

Thus, since, if the operator opens the lid portion 3, resets the endoscope 201 in the cleaning/disinfecting tank 4 and closes the lid portion 3, the warning is stopped, it becomes easy to perform the work of resetting the endoscope 201. Further, since the warning is continued unless the lid portion 3 is closed, it is possible to prevent an endoscope which has not been cleaned/disinfected from being taken out or used.

Figure 8:
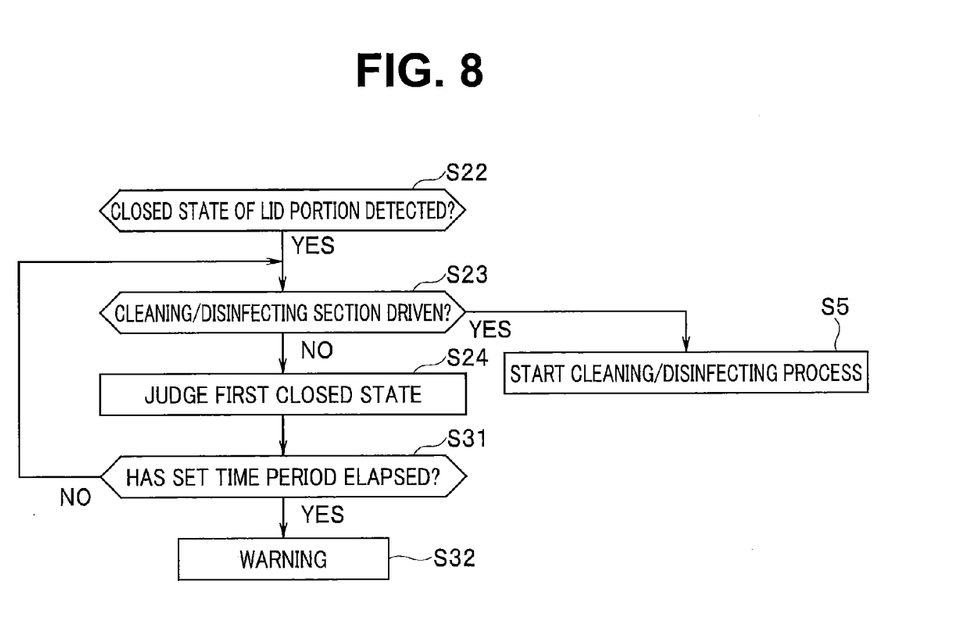
FIG. 8 is a flowchart showing a variation of controlling operation for the warning section by the control section of FIG. 2 in a case where a set time period elapses after a first closed state judging step of FIG. 6.

Further, another variation will be shown below with use of FIG. 8. FIG. 8 is a flowchart showing a variation of controlling operation for the warning section by the control section of FIG. 2 in a case where a set time period elapses after a first closed state judging step of FIG. 6.

If a time period until the cleaning/disinfection detecting section 105 detecting driving of the cleaning/disinfecting section 106 after the judging section 102 judging the first closed state exceeds a set time period, the control section 101 may perform drive control of the informing section 107.

More specifically, as shown in FIG. 8, at step S31 to which the process transitions after the first closed state judgment by the judging section 102 at step S24, the control section 101 judges whether the set time period until driving of the cleaning/disinfecting section 106 at step S23 performed by the cleaning/disinfecting process start button 7s being pressed on has elapsed or not. Note that the set time period may be arbitrarily changeable by the operator.

Furthermore, if the set time period has elapsed, the control section 101 transitions to step S32 and issues a warning by driving the informing section 107.

Thus, when the operator accommodates the endoscope 201 which has been used in the cleaning/disinfecting tank 4, and leaves the endoscope 201 as it is after closing the lid portion 3, forgetting to press the cleaning/disinfecting process start button 7s, a warning is issued from the informing section 107. Therefore, the operator can easily recognize that he/she forgot to press the cleaning/disinfecting process start button 7s.

That is, it is possible to prevent it from happening that it is forgotten to press the cleaning/disinfecting process start button 7s, the endoscope 201 which has not been cleaned/disinfected is left as it is in the cleaning/disinfecting tank 4 for a long time period, and the endoscope 201 which has not been cleaned/disinfected is taken out by another operator.

Note that other advantages are similar to those of the present embodiment described above.

Second Embodiment

Figure 9:
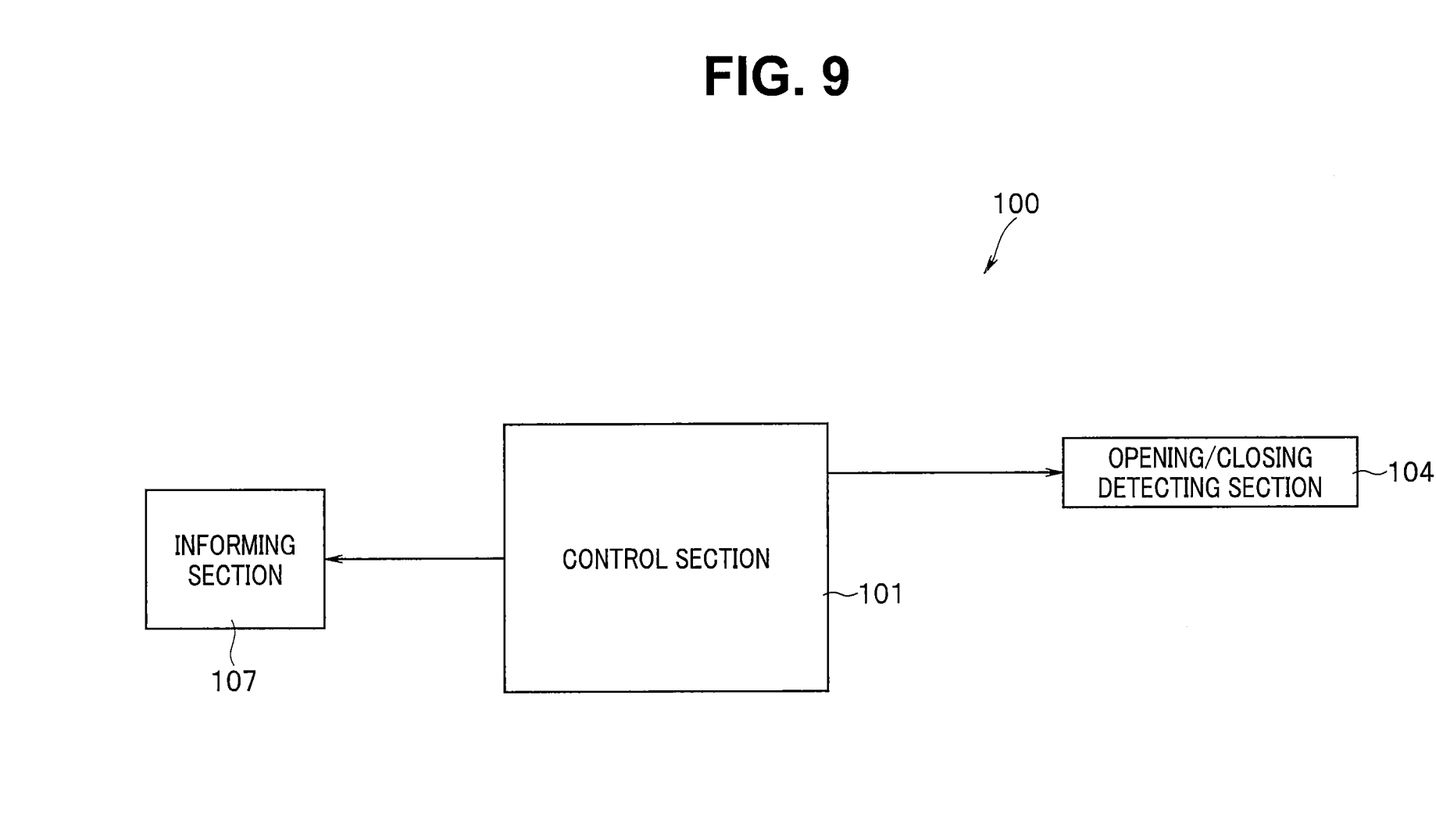
FIG. 9 is a block diagram schematically showing a warning section in an apparatus body of an endoscope cleaning/disinfecting apparatus of the present embodiment.
Figure 10:
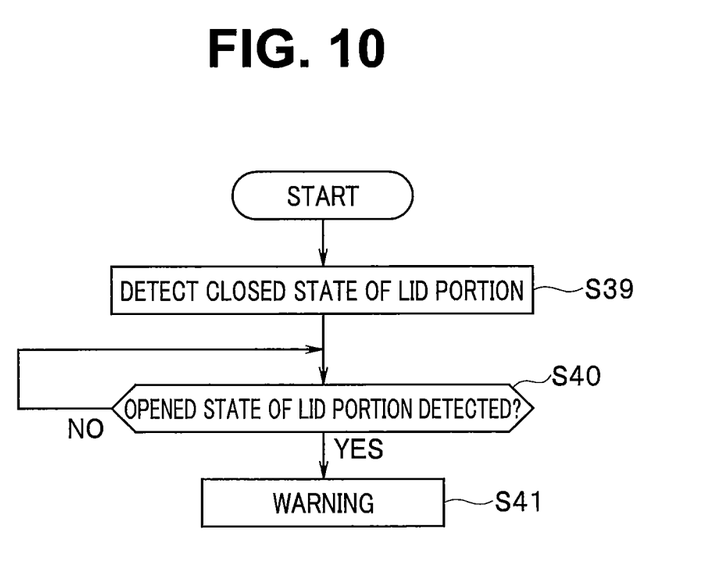
FIG. 10 is a flowchart showing controlling operation for a warning section by a control section of FIG. 9.

FIG. 9 is a block diagram schematically showing a warning section in an apparatus body of an endoscope cleaning/disinfecting apparatus of the present embodiment. FIG. 10 is a flowchart showing controlling operation for a warning section by a control section of FIG. 9.

In comparison with the endoscope cleaning/disinfecting apparatus of the first embodiment described above, the endoscope cleaning/disinfecting apparatus of the second embodiment is different in a point that the accommodation detecting section and the judging section are not provided and in a point that the control section performs drive control of an informing section if a lid portion is in an opened state.

Therefore, description will be made only on the different points, and components similar to those of the first embodiment are given same reference numerals, and description thereof will be omitted.

In the first embodiment described above, it is shown that the endoscope cleaning/disinfecting apparatus 1 has the accommodation detecting section 103 and the judging section 102; and, if it is detected by the accommodation detecting section 103 that the endoscope 201 is accommodated in the cleaning/disinfecting tank 4, and it is detected by the opening/closing detecting section 104 that the lid portion 3 is opened before driving of the cleaning/disinfecting section 106 in the first state judged by the judging section 102 by the closed state of the lid portion 3 being detected by the opening/closing detecting section 104, the control section 101 drives the informing section 107 to issue a warning.

This is not limiting. The control section 101 may drive the informing section 107 to issue a warning whenever the opening/closing detecting section 104 detects the opened state of the lid portion 3.

More specifically, as shown in FIG. 9, the warning section 100 may be configured only with the control section 101, and the opening/closing detecting section 104 and the informing section 107 each of which is connected to the control section 101.

Further, as shown in FIG. 10, the control section 101 may detect the opened state of the lid portion 3 using the opening/closing detecting section 104 at step S40 in a state that the opening/closing detecting section 104 detects the closed state of the lid portion 3 at step S39, and, if the opened state of the lid portion 3 is detected, issue a warning sound or a warning display to warn the operator that the lid portion 3 has been opened by driving the informing section 107 at step S41 lastly.

According to such a configuration, a warning is issued if the opened state of the lid portion 3 is detected irrespective of whether the endoscope 201 is accommodated in the cleaning/disinfecting tank 4 or not. Therefore, since the operator necessarily has to open the lid portion 3 in order to take out the endoscope 201 which has not been cleaned/disinfected, from the cleaning/disinfecting tank 4, it is possible to prevent the endoscope 201 which has not been cleaned/disinfected from being taken out.

Note that other components and advantages are similar to those of the first embodiment described above.

What is claimed is:

1. An endoscope cleaning/disinfecting apparatus comprising:
   a cleaning/disinfecting tank in which an endoscope is accommodated;
   a lid portion openable/closable relative to the cleaning/disinfecting tank;
   an accommodation detecting section detecting that the endoscope is accommodated in the cleaning/disinfecting tank;
   an opening/closing detecting section detecting an opened state and a closed state of the lid portion relative to the cleaning/disinfecting tank;
   a cleaning/disinfecting section for performing cleaning/disinfection of the endoscope in the cleaning/disinfecting tank;
   a cleaning/disinfection detecting section detecting driving of the cleaning/disinfecting section;
   an informing section issuing a warning;
   a judging section connected to the accommodation detecting section, the opening/closing detecting section and the cleaning/disinfection detecting section, the judging section judging a case where the opening/closing detecting section detects the closed state of the lid portion before the cleaning/disinfection detecting section detects driving of the cleaning/disinfecting section and after the accommodation detecting section detects that the endoscope is accommodated in the cleaning/disinfecting tank as a first closed state; and
   a control section connected to at least the opening/closing detecting section, the cleaning/disinfection detecting section, the informing section and the judging section, the control section performing control of driving the informing section to issue a warning when the opening/closing detecting section detects the opened state of the lid portion before the cleaning/disinfection detecting section detects driving of the cleaning/disinfecting section after the judging section detects the first closed state.

2. The endoscope cleaning/disinfecting apparatus according to claim 1, wherein the control section performs drive control of the informing section if a time period until the cleaning/disinfection detecting section detects driving of the cleaning/disinfecting section after the judging section judges the first closed state exceeds a set time period.

* * * * *